(12) United States Patent
Song et al.

(10) Patent No.: US 10,759,811 B2
(45) Date of Patent: Sep. 1, 2020

(54) METHOD OF PREPARING ANHYDROSUGAR ALCOHOL BY TWO-STEP REACTION

(71) Applicant: SK Innovation Co., Ltd., Seoul (KR)

(72) Inventors: In Hyoup Song, Daejeon (KR); Tae Seung Kim, Yongin-si (KR); Sung Real Son, Daejeon (KR); Yoon Jae Yim, Sejong-si (KR); Suk Joon Hong, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 15/246,954

(22) Filed: Aug. 25, 2016

(65) Prior Publication Data

US 2017/0057974 A1 Mar. 2, 2017

(30) Foreign Application Priority Data

Aug. 26, 2015 (KR) .................. 10-2015-0120482

(51) Int. Cl.
*C07D 493/04* (2006.01)
(52) U.S. Cl.
CPC .................. *C07D 493/04* (2013.01)
(58) Field of Classification Search
CPC .................................... C07D 493/04
USPC ....................................... 549/464
See application file for complete search history.

(56) References Cited

U.S. PATENT DOCUMENTS

| 6,013,812 A | 1/2000 | Haas et al. |
| 6,639,067 B1 | 10/2003 | Brinegar et al. |
| 7,615,652 B2 | 11/2009 | Holladay et al. |

FOREIGN PATENT DOCUMENTS

| KR | 101376481 B1 | 3/2014 | |
| WO | 03/089445 A2 | 10/2003 | |
| WO | WO 2012/081785 A1 * | 6/2012 | ............. C07C 29/80 |

OTHER PUBLICATIONS

Fleche et al., "Isosorbide. Preparation, Properties and Chemistry", Lecture at the 36th Starch Convention of the Arbeitsgemeinschaft Getreideforschung at Delmod, Apr. 24-26, 1985, pp. 26-30.
Menegassi De Almeida et al., "Cellulose Conversion to Isosorbide in Molten Salt Hydrate Media", ChemSusChem, Feb. 2010, pp. 325-328, vol. 3.
Bar et al.; "Sugar Alcohols"; Ullmann's Encyclopedia of Industrial Chemistry; 2012; pp. 1-37.
Li et al., "Sorbitol dehydration into isosorbide in a molten salt hydrate medium", Catal. Sci. Technol., 2013, pp. 1540-1546, vol. 3, RSC Publishing.

* cited by examiner

*Primary Examiner* — Yevgeny Valenrod
(74) *Attorney, Agent, or Firm* — The Webb Law Firm

(57) ABSTRACT

The present invention provides a method for preparing anhydrosugar alcohol, in which the reaction temperature in a vacuum reaction that converts sugar alcohol into anhydrosugar alcohol is controlled to two steps of temperature that is, a first-step low reaction temperature of 100 to 150° C. and a second-step high reaction temperature of 151 to 240° C., so that the selectivity for the intermediate product 1,4-sorbitan can be increased, thereby increasing the yield of anhydrosugar alcohol.

6 Claims, No Drawings

METHOD OF PREPARING ANHYDROSUGAR ALCOHOL BY TWO-STEP REACTION

CROSS-REFERENCE TO RELATED APPLICATION

This application claims priority to Korean Patent Application No. 10-2015-0120482 filed Aug. 26, 2015, the disclosure of which is hereby incorporated in its entirety by reference.

TECHNICAL FIELD

The present invention relates to a method for preparing anhydrosugar alcohol, and more particularly, to a method for preparing anhydrosugar alcohol, in which the reaction temperature in a vacuum reaction that converts sugar alcohol into anhydrosugar alcohol is controlled to two steps of temperature so that the yield of anhydrosugar alcohol can be economically increased.

BACKGROUND ART

Due to the exhaustion of traditional energy sources together with an increase in the global energy demand, impetus is currently being given to the development of alternative energy sources. Among them, biomass is renewable biological resources that attract a great deal of attention.

Among biomass-based industrial raw materials, isosorbide ($C_6H_{10}O_4$) that is prepared by dehydration of sorbitol ($C_6H_{14}O_6$) attracts attention as an environmentally friendly raw material for preparing polycarbonate (PC) as a substitute for bisphenol A (BPA), an epoxy monomer or an environmentally friendly plasticizer. Namely, isosorbide, a material that can be obtained by simple dehydration of sorbitol, is attracting attention as a monomer required for synthesis of next-generation, high-performance, environmentally friendly materials that can replace conventional polymer products, and many studies thereon have been conducted.

Environmentally friendly materials generally show poor properties compared to petrochemical-based materials, whereas isosorbide advantages in that it is environmentally friendly and, at the same time, shows excellent properties compared to conventional petrochemical-based materials. In addition, isosorbide that is also used as an agent for treating cardiac diseases may also be used as an additive that can make plastic materials stronger and tougher.

When D-glucose obtained from biomass by pretreatment is hydrogenated in the presence of a catalyst, sorbitol is produced. Isosorbide is produced by double dehydration of sorbitol. This cyclization reaction is influenced by various reaction conditions, including temperature, pressure, solvent, catalyst, etc.

Currently, as a method of preparing isosorbide from sorbitol, a process (Roquette process (France): G. Fleche, M. H. Lestrem, starch/starke 1986, 38, 26-30) is widely used in which sulfuric acid is used as a catalyst and a reaction is carried out under a reduced pressure of about 10 mmHg. However, when a liquid strong acid catalyst such as sulfuric acid is used, a reactor is easily corroded, and for this reason, an expensive reactor should be used. In addition, an additional process such as pH neutralization is required, and it is difficult to treat waste. Furthermore, a large amount of energy is continuously consumed to maintain a high vacuum level of about 10 mmHg, and thus the operating cost for the reaction is high. For this reason, a method employing molten salt hydrate (ChemSusChem. 2010, 3, 325-328) and the like have recently been proposed. However, this preparation method has problems in that, because molten salt hydrate should be used in very large amounts compared to the reactant sorbitol, the method is cost-ineffective and is not easy to commercialize.

In addition, to separate the prepared isosorbide, a vacuum distillation process is frequently used. Because isosorbide has a high boiling point and is easily decomposed or denatured by heat at high temperatures, it is difficult to separate by general atmospheric pressure distillation. For this reason, isosorbide is separated by distilling the reaction product at a relatively low temperature of about 150-220° C. under a vacuum of about 1-10 mmHg. Thus, various preparation methods have been developed in which reaction and distillation can be simultaneously performed in view of the efficiency of the reaction and separation processes.

Thus, if an efficient method for preparing and separating isosorbide is developed and a mass production process based on this method is provided so that a sufficiently inexpensive raw material (isosorbide) can be obtained, the demand for isosorbide as an industrial product can be increased.

Accordingly, the present inventors have found that, when the reaction temperature in a reaction that converts sorbitol into isosorbide is controlled to two steps of temperature (that is, a first-step low reaction temperature of 100-150° C. and a second-step high reaction temperature of 151-240° C.) in order to increase the selectivity for the intermediate product 1,4-sorbitan ($C_6H_{12}O_5$, 1,4-anhydro-sorbitol, 1,4-AHSO), the yield of isosorbide can be increased, thereby completing the present invention.

SUMMARY OF INVENTION

It is an object of the present invention to provide a method for preparing anhydrosugar alcohol, which can economically increase the yield of anhydrosugar alcohol in a reaction that converts sugar alcohol into anhydrosugar alcohol.

To achieve the above object, the present invention provides a method for preparing anhydrosugar alcohol, in which an aqueous solution of sugar alcohol is subjected to a first-step reaction at a temperature of 100 to 150° C. in the presence of a catalyst, and then subjected to a second-step reaction at a temperature of 151 to 240° C.

DETAILED DESCRIPTION OF THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

In the present invention, when the reaction temperature in a reaction that converts sorbitol into isosorbide was controlled to two steps of temperature (that is, a first-step low reaction temperature of 100-150° C. and a second-step high reaction temperature of 151-240° C.) in order to increase the selectivity for the intermediate product 1,4-sorbitan, the yield of isosorbide could be increased.

A reaction that produces isosorbide by dehydration of sorbitol is shown in the following Reaction Scheme 1:

Reaction Scheme 1

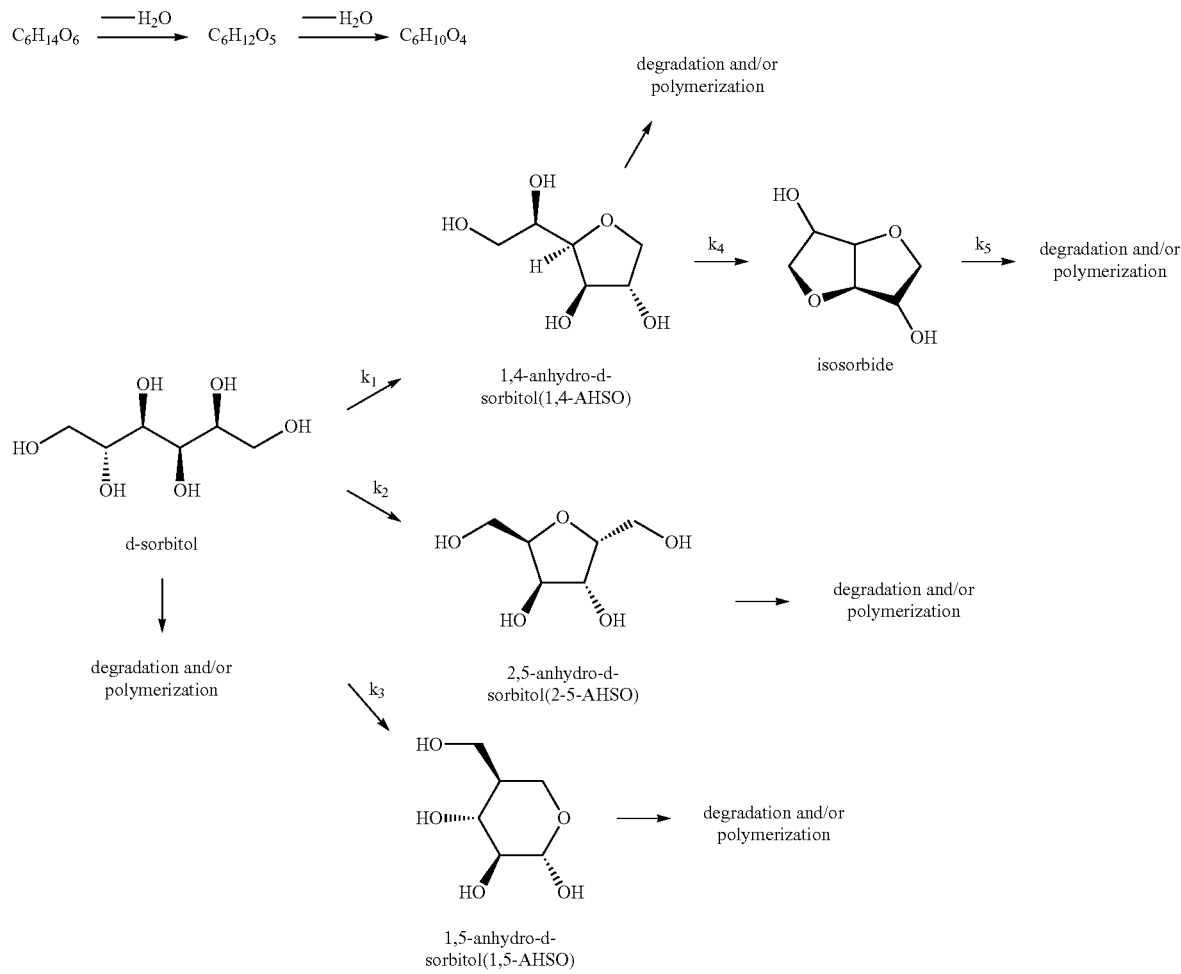

In reaction scheme 1 above, a preferred path consists of a two-step reaction in which one water molecule is removed from D-sorbitol to produce 1,4-sorbitan, after which one water molecule is removed from 1,4-sorbitan to produce D-isosorbide.

In the dehydration reaction process in which sorbitan is produced from sorbitol, i) 1,4-sorbitan is produced within a short time at a relatively low temperature (100 to 150° C.), and ii) 2,5-sorbitan is produced over a long time at a temperature higher than 1,4-sorbitan. Other sorbitan isomers are produced at relatively low rates.

The temperature at which the production of 1,4-sorbitan is promoted is preferably 100 to 150° C., whereas a temperature of 170° C. or higher is required to volatilize the produced isosorbide at a pressure of about 10 mmHg. When the produced isosorbide stays in the reactors for a long time without being volatilized, it is modified into other substances. Thus, in order to increase the selectivity for 1,4-sorbitan and increase the yield of isosorbide that is produced therefrom, an operating method capable of all these requirements is required.

Therefore, the present invention is directed to a method for preparing anhydrosugar alcohol, in which an aqueous solution of sugar alcohol is subjected to a first-step reaction at a temperature of 100 to 150° C. in the presence of a catalyst, and then subjected to a second-step reaction at a temperature of 151 to 240° C.

In the present invention, sorbitol and a catalyst are introduced into a first-step reactor. In order to maximize the selectivity for 1,4-sorbitan, the introduced sorbitol is reacted at a pressure of 1-200 mmHg, preferably 3-100 mmHg, more preferably 5-40 mmHg, and a temperature of 100 to 150° C. In addition, the residence time in the first-step reactor is 10-300 minutes so that the conversion rate of sorbitol reaches 50% or more, preferably 75% or more.

The reaction solution in the first-step reaction is continuously introduced and reacted in a second-step reactor which is maintained at a temperature of 151 to 240° C., so that the produced isosorbide can be volatilized in the reactor after production. The reaction in the second-step reactor is performed at a pressure of 1-200 mmHg, preferably 3-100 mmHg, more preferably 5-40 mmHg, and a temperature of 151 to 240° C., and the residence time in the second-step reactor is 10-180 minutes.

The temperature of the first-step reaction may preferably range from 100° C. to 150° C., and the temperature of the second-step reaction may range from 151° C. to 240° C. In this temperature range, the effect of increasing the yield of isosorbide is obtained. In addition, the temperature difference between the first-step reaction and the second-step reaction is preferably 50° C. to 120° C.

If the temperature of the first-step reaction is lower than 100° C., the reaction time or the residence time will be very long, and if the temperature of the first-step reaction is higher than 150° C., side reactions can be promoted to reduce the yield of isosorbide. Meanwhile, if the temperature of the second-step reaction is lower than 151° C., the reaction for the conversion of 1,4-sorbitan to isosorbide will not be sufficiently performed, and if the temperature of the second-step reaction is higher than 240° C., side reactions in which 1,4-sorbitan or the produced isosorbide is degraded, modified or polymerized will strongly occur so that the yield of isosorbide can decrease rather than increase.

In the present invention, the time of the first-step reaction may be 10-300 minutes, and the time of the second-step reaction may be 10-180 minutes. In the first-step reaction, sorbitol is allowed to react in the forward direction at a low temperature without producing by-products, and in the second-step reaction, the product of the first-step reaction is exposed to a high temperature for a short time so that it will not produce other by-products. Thus, the first-step reaction may be performed for the time during which the starting material sorbitol is completely converted, and the second-step reaction may be performed for the time during which a sufficient amount of isosorbide can be volatilized.

In the present invention, the anhydrosugar alcohol may be isosorbide, and the sugar alcohol may be sorbitol.

The preparation method according to the present invention may be performed in a continuous stirred tank reactor (CSTR), a plug flow reactor (PFR), a trickle bed reactor (TBR) or a batch reactor (BR). In other words, the first-step and second-step reactors may be operated in a state in which they are connected to each other. Alternatively, the reactions may also be performed in a batch fashion. If the preparation method according to the present invention is performed using a batch reactor, sorbitol may be reacted in a single reactor at the first-step reaction temperature, and then the temperature of the reactor may be increased to the second-step reaction temperature so that the second-step reaction may be performed continuously following the first-step reaction. The reaction time in the batch reaction can be controlled by controlling the times during which the first-step and second-step reaction temperatures are maintained.

The second-step reactor may be operated continuously after the first-step reaction is completed in a batch fashion. If the two reactors are continuously operated, the solution from the outlet of the second-step reactor may be recycled to either the inlet of the second-step reactor or the inlet of the first-step reactor in order to increase the yield of isosorbide.

In the continuous operation or batch operation in the first-step and second-step reactors, steam, nitrogen or a mixture of the two gases may be introduced to increase the recovery of isosorbide.

Regarding selection of the type of first-step or second-step reactor, the second-step reactor that is used in the present invention may be selected from among a continuous stirred tank reactor (CSTR), a thin film evaporator reactor, a kneader reactor, a vacuum dryer reactor, a finisher reactor, a distillation tower, and the like, regardless of the type of first-step reactor. When the process for preparing isosorbide is performed in two divided steps as described above, the reaction that requires a long time may be performed in the first-step reactor so that the reaction time in the second-step reactor can be reduced. Thus, the equipment cost can be significantly reduced, and the production cost can also be reduced.

The volatilized isosorbide vapor and steam are condensed in a condenser to form a liquid which is then recovered. Herein, the condenser is maintained at a temperature between −40 and 100° C. so that the content of isosorbide in the condensed mixture is controlled to 50-99 wt %.

The isosorbide product obtained as described above has a purity of 90-99% on a dry weight basis, and is obtained in a yield higher than those prepared by conventional direct high-temperature distillation methods.

Meanwhile, U.S. Pat. No. 7,615,652 discloses the preparation of isosorbide by a two-step reaction. However, in this US Patent, a solid acid catalyst (heterogeneous catalyst) is used in the first-step reactor, and thus severe inactivation of the catalyst by coking during the reaction occurs. For this reason, for a continuous process, a process for replacing the catalyst at very short time intervals or a process for regenerating the catalyst is necessarily required. Thus, operating costs for this catalyst replacement or regeneration process are incurred. In the present invention, a homogeneous catalyst is used, and thus the above-described problems can be overcome and a smooth continuous process can be operated.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1

Control of Temperature to Two Steps of Temperature

A first-step reaction was performed in a 250-mL round-bottom flask (RBF). Specifically, 70 g of D-sorbitol (Aldrich) was introduced into the RBF and heated to a 130° C. (that is a first-step reaction temperature) so as to be dissolved, and then 0.5 g of naphthalenesulfonic acid was added thereto. Then, the solution was reacted with stirring at a pressure of 10 mmHg for 2 hours.

After completion of the first-step reaction, to perform a second-step reaction, the content in the RBF reactor was heated to 180° C. (that is a second-step reaction temperature) while maintaining the reaction pressure, and under such conditions, the second-step reaction was performed for 1 hour.

The obtained reaction product was diluted 20-fold with water and analyzed by high-performance liquid chromatography (HPLC, Agilent; equipped with a carbohydrate column).

Example 2

Control of Temperature to Two Steps of Temperature

The process of Example 1 was repeated, except that a second-step reaction temperature of 200° C. was used instead of 180° C.

Example 3

Control of Temperature to Two Steps of Temperature

The process of Example 2 was repeated, except that a first-step reaction temperature of 110° C. was used instead of 130° C.

Comparative Example 1

Isothermal Reaction

To perform a reaction at a single temperature, 70 g of D-sorbitol (Aldrich) was introduced into a 250-mL RBF and heated to a 130° C. so as to be dissolved, and then 0.5 g of naphthalenesulfonic acid was added thereto. Then, the solution was reacted with stirring at a pressure of 10 mmHg for 2 hours.

The obtained reaction product was analyzed in the same manner as described in Example 1.

Comparative Example 2

Isothermal Reaction

The process of Comparative Example 1 was repeated, except that a reaction temperature of 180° C. was used instead of 130° C.

Comparative Example 3

Heterogeneous Catalytic Reaction

The process of Example 3 was repeated, except that the heterogeneous catalyst sulfated $ZrO_2$ was used instead of the homogeneous catalyst naphthalenesulfonic acid.

The yields of the products obtained in Examples 1 to 3 and Comparative Examples 1 to 3 are shown in Tables 1 to 3 below.

TABLE 1

| | First-step reaction temp. (° C.) | Second-step reaction temp. (° C.) | Amount of ISB remaining in distillate (wt %) | Amount of ISB remaining in residue (wt %) | Total amount of ISB (wt %) |
|---|---|---|---|---|---|
| Example 1 | 130 | 180 | 59.53 | 0.20 | 59.73 |
| Example 2 | 130 | 200 | 60.58 | 0.16 | 60.74 |
| Example 3 | 110 | 200 | 63.52 | 0.10 | 63.62 |

TABLE 2

| | Reaction temp. (° C.) | Amount of ISB remaining in distillate (wt %) | Amount of ISB remaining in residue (wt %) | Total amount of ISB (wt %) |
|---|---|---|---|---|
| Comp. Ex. 1 | 130 | 4.20 | 41.87 | 46.07 |
| Comp. Ex. 2 | 180 | 53.40 | 0.35 | 53.75 |

As can be seen in the above tables, the yields of the isosorbides prepared in Examples 1 to 3 using the two-step temperature control were significantly higher than the yields of those prepared in Comparative Examples 1 and 2 using the isothermal reaction. Because the ratio of the raw cost of sorbitol to the production cost of isosorbide is about 50% or more, it can be seen that an increase in yield of up to 17.6 wt % during a short reaction time of about 40% can ensure higher productivity, indicating that a significant economic gain is obtained.

TABLE 3

| | First-step reaction temp. (° C.) | Second-step reaction temp. (° C.) | Amount of ISB remaining in distillate (wt %) | Amount of ISB remaining in residue (wt %) | Total amount of ISB (wt %) |
|---|---|---|---|---|---|
| Comp. Ex. 3 | 110 | 200 | 53.09 | 0.24 | 53.33 |

As shown in Table 3 above, the yields of the isosorbides prepared in the Examples using the homogeneous catalyst naphthalenesulfonic acid were significantly higher than the yield of the isosorbide prepared in Comparative Example 3 using the heterogeneous catalyst.

INDUSTRIAL APPLICABILITY

As described above, in the method for preparing anhydrosugar alcohol according to the present invention, the yield of anhydrosugar alcohol can be increased. Furthermore, the reaction for preparing anhydrosugar alcohol is performed in two steps such that a reaction step that requires a long time is performed in the first-step reactor, and thus the reaction time in the second-step reactor can be reduced and the equipment cost can be considerably reduced, thereby reducing the production cost. In addition, because the homogeneous is used, a smooth continuous process can be operated without having to add a process of replacing the catalyst at very short time intervals or a process of regenerating the catalyst.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of preparing anhydrosugar alcohol comprising:
   subjecting to a first-step dehydration reaction of an aqueous solution of sugar alcohol at a temperature of 100 to 150° C. in the presence of a catalyst and then subjecting to a second-step dehydration reaction at a temperature of 151 to 240° C.,
   wherein the first-step dehydration reaction and the second-step dehydration reaction are performed at a pressure of greater than 5 mmHg to less than or equal to 200 mmHg.

2. The method of claim 1, wherein the catalyst is a homogeneous catalyst.

3. The method of claim 1, wherein the first-step reaction and the second-step reaction are performed for 10-300 minutes and 10-180 minutes, respectively.

4. The method of claim 1, wherein the anhydrosugar alcohol is isosorbide, and the sugar alcohol is sorbitol.

5. The method of claim 1, which is performed in a continuous stirred tank reactor (CSTR), a plug flow reactor (PFR), a trickle bed reactor (TBR) or a batch reactor (BR).

6. The method of claim 1, wherein the second-step reaction product is collected by being condensed to liquid in a condenser maintained at a temperature of -40 to 100° C.

* * * * *